United States Patent
Spragia et al.

(12) 
(10) Patent No.: US 6,245,816 B1
(45) Date of Patent: Jun. 12, 2001

(54) BENZOYLPHENYLUREA INSECTICIDES AND METHODS OF USING CERTAIN BENZOYLPHENYLUREAS TO CONTROL ANTS

(76) Inventors: Ronald J. Spragia, P.O. Box 1671, Placerville, CA (US) 95667; George W. Johnson, 6715 Knollcreek Dr., Indianapolis, IN (US) 46256; Laura L. Karr, 800 N. 200 E., Lebanon, IN (US) 46052; Jeff M. Edwards, Rte. 1, Box 47, Torrington, WY (US) 82240; Brian M. Schneider, 75 Red Oak La., Carmel, IN (US) 46033

( * ) Notice: Subject to any disclaimer, the term of this patent is extended or adjusted under 35 U.S.C. 154(b) by 0 days.

(21) Appl. No.: 09/534,741

(22) Filed: Mar. 24, 2000

Related U.S. Application Data

(63) Continuation of application No. 09/189,967, filed on Nov. 10, 1998, which is a continuation of application No. 08/963,506, filed on Nov. 3, 1997, now Pat. No. 5,886,221
(60) Provisional application No. 60/069,881, filed on Nov. 8, 1996.

(51) Int. Cl.$^7$ .......................... A01N 47/28; C07C 275/54
(52) U.S. Cl. .............................. 514/594; 564/44
(58) Field of Search ................ 514/594; 564/44

(56) References Cited

U.S. PATENT DOCUMENTS

| | | | |
|---|---|---|---|
| 3,748,356 | 7/1973 | Wellinga et al. | 260/553 E |
| 4,468,405 | 8/1984 | Rigterink et al. | 424/322 |
| 4,798,837 | 1/1989 | Drabek et al. | 514/594 |
| 4,925,875 | 5/1990 | Drabek | 514/594 |
| 4,925,876 | 5/1990 | Drabek | 514/594 |
| 4,973,589 | 11/1990 | Barnett et al. | 514/245 |
| 5,132,325 | 7/1992 | Drabek et al. | 514/594 |
| 5,153,224 | 10/1992 | Drabek et al. | 514/594 |
| 5,288,756 | 2/1994 | Drabek et al. | 514/594 |
| 5,300,293 | 4/1994 | Minagawa et al. | 424/405 |
| 5,416,102 | 5/1995 | Barnett et al. | 514/351 |
| 5,556,883 | 9/1996 | Thoms et al. | 516/594 |
| 5,886,221 | 3/1999 | Sbragia et al. | 514/594 |

FOREIGN PATENT DOCUMENTS

| | | |
|---|---|---|
| 68094/87 | 8/1987 | (AU) . |
| 87/71748 | 10/1987 | (AU) . |
| 3827133 A1 | 2/1989 | (DE) . |
| 194688 | 9/1986 | (EP) . |
| 221847 A2 | 5/1987 | (EP) . |
| 243790 | 11/1987 | (EP) . |
| 263438 A2 | 4/1988 | (EP) . |
| 290392 A1 | 11/1988 | (EP) . |
| 2166134 | 4/1986 | (GB) . |
| WO 94/03066 | 2/1994 | (WO) . |
| WO 95/16354 | 6/1995 | (WO) . |
| WO 97/40689 | 11/1997 | (WO) . |

OTHER PUBLICATIONS

Journal of Economic Entomology (Oct. 1996), vol. 89, No. 5, pp. 1156–1160, Nan–Yao Su and Rudolf H. Scheffrahn, "Comparative Effects of Two Chitin Synthesis Inhibitors, Hexaflumuron and Lufenuron, in a Bait Matrix Against Subterranean Termites (Isoptera: Rhinotermitidae)".

Doppelreiter et al., *Entwicklungshemmung durch Diflubenzuron bei den Bodentermiten Heterotermes indicola und Reticulitermes flavipes, Z. ang. Ent.* 91, Verlan Paul Parcy, Hamburg und Berlin, (1982), 131–37.

*Primary Examiner*—Peter O'Sullivan
(74) *Attorney, Agent, or Firm*—Carl D. Corvin

(57) ABSTRACT

Compounds of the formula (I)

(I)

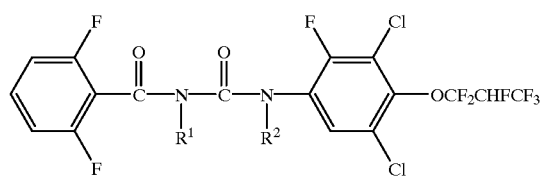

wherein R$^1$ and R$^2$ are H, methyl, or ethyl, have unexpected activity against ants. Compounds wherein at least one of R$^1$ and R$^2$ is methyl or ethyl are novel.

4 Claims, No Drawings

BENZOYLPHENYLUREA INSECTICIDES AND METHODS OF USING CERTAIN BENZOYLPHENYLUREAS TO CONTROL ANTS

RELATED APPLICATIONS

This application is a continuation of application Ser. No. 09/189,967, which has a filing date of Nov. 10, 1998, and is now allowed. Application Ser. No. 09/189,967 is a continuation of application Ser. No. 08/963,506, which has a filing date of Nov. 3, 1997, and is now U.S. Pat. No. 5,886,221. Application Ser. No. 08/963,506, is an original application of provisional application Ser. No. 60/069,881 which has a filing date of Nov. 8, 1996. Provisional application serial number 60/069,881 is converted provisional application of original application serial number 08/745,387 which has a filing date of Nov. 8, 1996.

BACKGROUND OF THE INVENTION

This invention provides novel benzoylphenylurea insecticides and novel methods of inhibiting cockroaches, ants, fleas, and termites.

A broad class of benzoylphenylurea insecticides is disclosed in U.S. Pat. No. 3,748,356. European Patent Application 263438 discloses that certain N-substituted phenyl-N'-substituted benzoyl-N-methylureas are highly safe to beneficial aquatic Crustacea while exhibiting equal or superior insecticidal activities to non-alkylated analogs. Hexaflumuron, a commercially significant benzoylphenylurea, is disclosed in U.S. Pat. No. 4,468,405. Use of hexaflumuron in methods of controlling termites is disclosed in WO 93/24011. Use of hexaflumuron to control cockroaches is disclosed in WO 94/03066. The compound N-[3,5-dichloro-2-fluoro-4-(1,1,2,3,3,3-hexafluoropropoxy)phenyl]-N'-(2,6-difluorobenzoyl)urea is disclosed in DE 3827133 and European Patent Application A 243,790, but there was no disclosure of the unexpected activity of the compound against cockroaches, ants, fleas, and termites.

We have discovered that certain benzoylphenylurea compounds, some of which are novel, have substantially greater activity against cockroaches, ants, fleas, and termites than would have been expected based on comparison with the closest prior art, i.e., hexaflumuron. Another significant property of the novel compounds of the invention is their surprisingly low toxicity to Daphnia.

SUMMARY OF THE INVENTION

The invention provides a method of controlling cockroaches, ants, fleas, or termites which comprises delivering a effective amount of a compound of the formula (I):

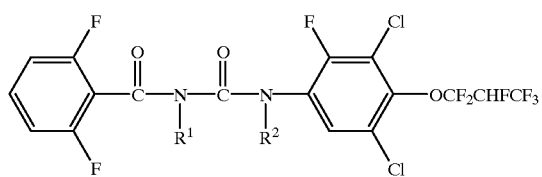

(I)

wherein $R^1$ and $R^2$ are H, methyl, or ethyl, to a location where control of cockroaches, ants, fleas, or termites is desired.

More specifically, the invention provides:

A method of controlling cockroaches which comprises a compound of the formula (I), in an amount effective to control cockroaches, to a location where control of cockroaches is desired;

A method of controlling ants which comprises delivering a compound of the formula (I), in an amount effective to control ants, to a location where control of ants is desired;

A method of controlling fleas which comprises delivering a compound of the formula (I), in an amount effective to control fleas, to a location where control of fleas is desired; and A method of controlling termites which comprises delivering a compound of the formula (I), in an amount effective to control termites, to a location where control of termites is desired.

The invention also provides novel compounds of the formula (II)

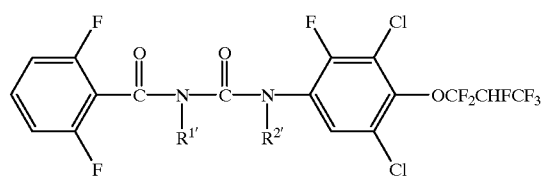

(II)

wherein $R^{1'}$ and $R^{2'}$ are H, methyl, or ethyl, provided that at least one of $R^{1'}$ and $R^{2'}$ is methyl or ethyl.

DETAILED DESCRIPTION OF THE INVENTION

Intermediate 1

2,6-difluorobenzoyl isocyanate

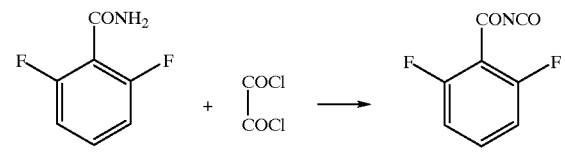

A mixture of 0.52 g of 2,6-difluorobenzamide and 0.33 ml of oxalyl chloride was stirred under reflux in 15 ml 1,2-dichloroethane overnight. Solvent was removed under vacuum and 10 ml 1,2-dichloroethane was added. Solvent was removed under vacuum to leave the title intermediate, which could be used directly or dissolved in 1,2-dichloroethane and stored for future use.

Intermediate 2

3,5-Dichloro-4-(1,1,2,3,3,3-hexafluoropropoxy)aniline

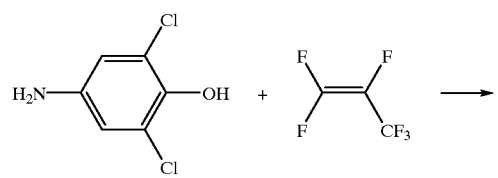

-continued

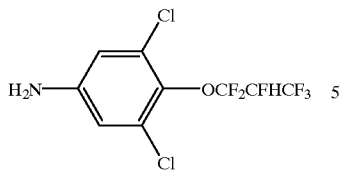

X522838

To a solution of 2.0 g of 4-amino-2,6-dichlorophenol in 40 mL tetrahydrofuran at room temperature was added 0.7 g of 87% potassium hydroxide. The mixture was warmed to 40° C. and stirred for 10 minutes, then chilled to 0° C. Hexafluoropropene was bubbled in for 5 minutes, and the mixture stirred at room temperature over night. It was then concentrated under vacuum to dryness. The residue was dissolved in 50 mL dichloromethane and washed with 20 mL brine solution. The organic layer was separated and filtered through phase separation filter paper and then concentrated under vacuum to an oil. This was diluted with 50 mL dichloromethane and 50 mL heptane and re concentrated to give 3.05 g of 3,5-dichloro-4-(1,1,2,3,3,3-hexafluoropropoxy)aniline as a brown oil. Proton and $^{19}$F nmr spectra were consistent with the proposed structure.

Intermediate 3

3,5-Dichloro-2-fluoro-4-(1,1,2,3,3,3-hexafluoropropoxy) aniline

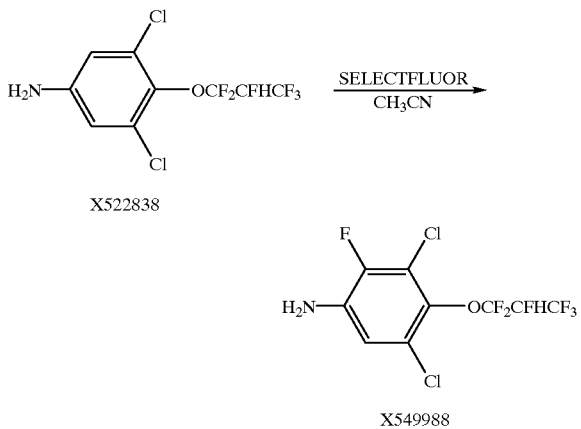

To a solution of 2.50 g 3,5-dichloro 4-(1,1,2,3,3,3-hexafluoropropoxy)aniline in 60 mL acetonitrile under an atmosphere of nitrogen at room temperature there was added 2.57 g 1-chloromethyl-4-fluoro-1,4-diazoniabicyclo[2.2.2] octane bis (tetrafluoroborate) SELECTFLUOR™ (Air Products) portion wise over a 10 minute period. The mixture was warmed to 70° C. over a one hour period, then cooled to room temperature and poured into 100 mL of saturated sodium bicarbonate solution. The product was extracted with 150 mL ethyl acetate. The organic layer was separated, washed with 50 mL of brine solution, separated, and dried over magnesium sulfate. The magnesium sulfate was removed by filtration, and the filtrate was concentrated under vacuum to give a dark oil 2.52 g. Thie product was chromatographed using a Michel-Miller low pressure silica gel column eluted with 6:1 heptane/ethyl acetate. Like fractions were pooled and concentrated under vacuum to a brown oil 1.19 g. The proton and $^{19}$F nmr spectra were consistent with the proposed structure. Anal. calcd $C_9H_4Cl_2F_7N_1O_1$: C, 31.24; H, 1.17; N, 4.05. Found: C, 31.52; H, 1.15; N, 4.02.

Intermediate 4

3,5-Dichloro-2-fluoro-4-(11 23,3,3-hexafluoropropoxy)-N-ethyl aniline

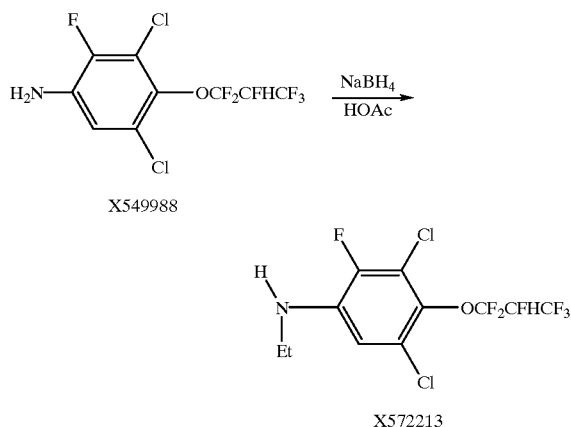

To a solution of 0.28 g 3,5-dichloro-2-fluoro-4-(1,1,2,3,3,3-hexafluoropropoxy) aniline in 8 mL glacial acetic acid at room temperature under an atmosphere of nitrogen was slowly added 0.31 g sodium borohydride. The addition was carried out over a 1.5 hour period through a solid addition funnel between 25–34° C. with ice water cooling. The mixture was stiired at room temperature over night. Then the reaction mixture was added to 80 mL water and the pH was carefully adjusted to 7 by adding solid sodium carbonate. The product was extracted with 80 mL ethyl acetate. The organic layer was separated, washed with brine solution, separated, and dried over magnesium sulfate. The magnesium sulfate was removed by filtration, and the filtrate was concentrated under vacuum to give a brown oil 0.29 g. The product was chromatographed using a Michel-Miller low pressure silica gel column eluted with 9:1 heptane/ethyl acetate. Like fractions were pooled and concentrated under vacuum to give 0.19 g of a tan oil. $^1$H-NMR d 1.28 (t, 3H), 3.17 (q, 4H), 3.95 (bs, 1H), 4.94–5.21 (md, 1H), 6.59 (d, 1H). Anal. calcd $C_{11}H_8Cl_2F_7N$: C, 35.31; H, 2.16; N, 3.74. Found: C, 35.32; H, 2.14; N, 3.74.

PREPARATION OF PRODUCTS

Compound 1

N-[3,5-Dichloro-2-fluoro-4-(1,1,2,3,3,3-hexafluoropropoxy)phenyl]-N'-(2,6-difluorobenzoyl)urea

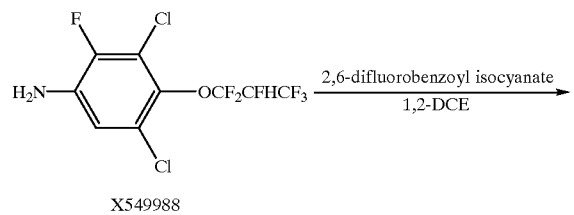

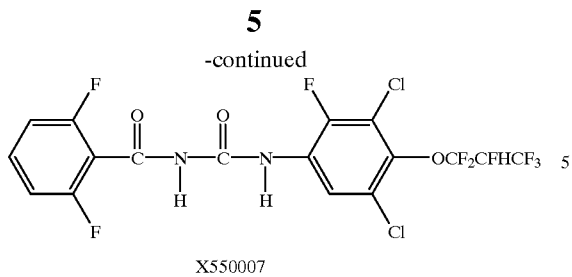

X550007

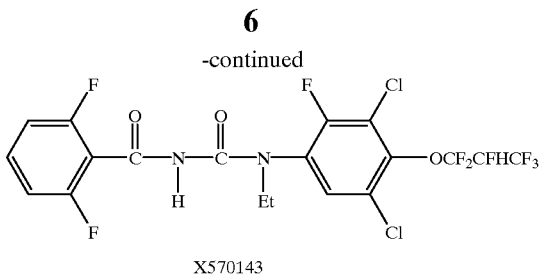

X570143

To a solution of 1.31 g 3,5-dichloro-2-fluoro-4-(1,1,2,3,3,3-hexafluoropropoxy) aniline in 5 mL 1,2-dichloroethane under an atmosphere of nitrogen at room temperature was added 0.87 g 2,6-difluorobenzoyl isocyanate dissolved in 10 mL dichloroethane dropwise over a 10 minute period. The mixture was stirred, warmed to 40° C. for a one hour period, then concentrated under vacuum to a brown solid 2.0 g. The mixture was chromatographed using a Michel-Miller low pressure silica gel column eluted with 4:1 dichloromethane/heptane. Like fractions were pooled and concentrated under vacuum to give 1.67 g of a light tan solid, mp 156–7° C. Proton and $^{19}$F nmr spectra were consistent with the proposed structure. Anal. calcd $C_{17}H_7Cl_2F_9N_2O_3$: C, 38.58; H, 1.33; N, 5.29. Found: C, 38.64; H, 1.40; N, 5.44.

Compound 2

N-[3,5-Dichloro-2-fluoro-4-(1,1,2,3,3,3-hexafluoropropoxy)phenyl]-N'-(2,6-difluorobenzoyl)-N-ethylurea To a solution of 1.00 g 3,5-dichloro-2-fluoro-4-(1,1,2,3,3,3-hexafluoropropoxy)-N-ethyl aniline in 2 mL 1,2-dichloroethane under an atmosphere of nitrogen at room temperature there was added 0.54 g 2,6-difluorobenzoyl isocyanate dissolved in 6 mL dichloroethane dropwise over a 10 minute period. The mixture was stirred and warmed to 40° C. for a 1.5 hour period. Analysis by thin layer chromatography silica gel 4:1 heptane/ethyl acetate indicated incomplete reaction. To the mixture was added 0.13 g 2,6-difluorobenzoyl isocyanate in 1.5 mL 1,2-dichloroethane, and the mixture was warmed at 40° C. for 2.5 hour. Analysis by TLC indicated complete reaction. The reaction mixture was concentrated under vacuum to give an oil 1.64 g, which was chromatographed using a Michel-Miller low pressure silica gel column eluted with 4:1 heptane/ethyl acetate. Like fractions were pooled and concentrated under vacuum to give a white solid 0.87 g, mp 106–14° C. Proton nmr and mass spectra were consistent with the proposed structure. Anal. calcd $Cl_{19}H_{11}Cl_2F_9N_2O_3$: C, 40.95; H, 1.99; N, 5.03. Found: C, 40.89; H, 1.92; N, 5.03.

Compound 3

N-[3,5-Dichloro-2-fluoro-4-(1,1,2,3,3,3-hexafluoropropoxy)phenyl]-N'-(2,6-difluorobenzoyl)-N'-ethyl urea

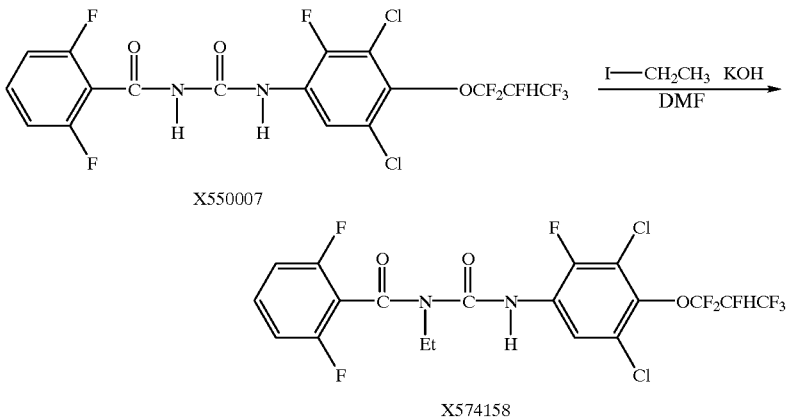

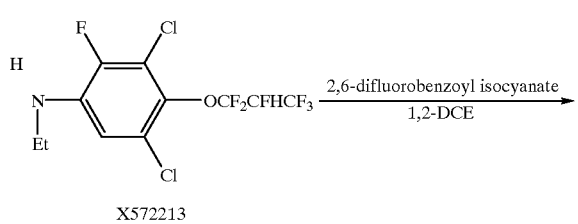

Dissolve 1.65 g N-[3,5-dichloro-2-fluoro-4-(1,1,2,3,3,3-hexafluoropropoxy)phenyl]-N'-(2,6-difluorobenzoyl) urea in 10 mL N,N-dimethylformamide and add 0.22 g 87% potassium hydroxide. Chill to 0° C. and add 0.97 g iodoethane. Stir at 0° C. for a 7 hour period. Store in freezer at 0° C. over night. Analysis by thin layer chromatography silica gel dichloromethane shows product forming with starting urea remaining. The reaction was treated as above at 0° C. for the next two days. Additional amounts of iodoethane, 1.94 g, and 0.10 g 87% potassium hydroxide were added. Pour reaction mixture into 50 mL brine solution and extract with 80 mL ethyl acetate. Separate organic layer and dry over magnesium sulfate. Filter drying agent and concentrate the filtrate under vacuum to a red oil 2.63 g. Chromatograph using a Michel-Miller low pressure silica gel column and elute with 2:1 heptane/dichloromethane. Pool like fractions and concentrate under vacuum to 0.18 g of a pink solid, mp 105–06° C. Proton nmr and mass spectra were consistent with the proposed structure. Anal. calcd $C_{19}H_{11}Cl_2F_9N_2O_3$: C, 40.95; H, 1.99; N, 5.03. Found: C, 40.99; H, 1.85; N, 4.98.

Biological Activity

German cockroach 2nd instars (*Blattella germanica*)

Continuous, low-dose ingestion exposure (treated cornmeal)

Rates: 0.19, 0.78, 3.12, 12.5, 50, 200 ppm

| Compound | $LC_{50}$ (ppm) | |
|---|---|---|
| | 21 days | 42 days |
| Compound 1 | <2.2 | <0.78 |
| Compound 2 | 0.35 | 0.26 |
| Compound 3 | 8.0 | 1.5 |
| hexaflumuron | >200 | >200 |

Under continuous exposure, Compounds 1, 2, and 3 were far more active than hexaflumuron.

German cockroach 2nd instars (*Blittella germanica*)

Limited ingestion exposure (48 hr) to treated cornmeal

Rates: 1, 10, 100, 1000, 10000 ppm

| Compound | $LC_{50}$ (ppm) | |
|---|---|---|
| | 21 days | 42 days |
| Compound 1 | <22.2 | <9.1 |
| Compound 2 | 21.1 | 12.8 |
| hexaflumuron | >10,000 | >10,000 |

Under limited exposure, Compounds 1 and 2 were more potent than hexaflumuron at both 21 and 42 days after exposure.

Cat Flea (*Ctenocephalides felis*)

Continuous exposure of larvae to treated media, impact on subsequent adult emergence Rates: 0.1, 1.0, 10, 100, 1000 ppm

| Compound | $LC_{50}$ (ppm) | $LC_{90}$ (ppm) |
|---|---|---|
| Compound 1 | 2.8 | 22 |
| Compound 2 | 12.7 | 18.6 |
| hexaflumuron | 65.7 | 333.5 |

Compounds 1 and 2 were both far more efficacious than hexaflumuron against cat fleas.

Subterranean Termite (*Reticulitermes flavipes*)

Continuous exposure (56 days) to treated paper

Rates: 0.78, 3.12, 12.5, 50, 200 ppm

| Compound | $LC_{50}$ (ppm) | | $LT_{50}$ (days) for |
|---|---|---|---|
| | 35 days | 56 days | 200 ppm trt |
| Compound 1 | 31.2 | <0.78 | 27.6 |
| Compound 2 | <0.78 | <0.78 | not calc. |
| hexaflumuron | >200 | 1.3 | 33.8 |

Under continuous exposure, Compounds 1 and 2 were more potent and quicker acting than hexaflumuron.

Subterranean Termite (*Reticulitermes flavipes*)

Limited exposure (7 days) with mortality determined at 14, 28, 42, and 56 days

| Compound | $LT_{50}$ (days) for 10000 ppm treatment |
|---|---|
| Compound 1 | 23.7 |
| hexaflumuron | 32.9 |

Under limited exposure, a high rate of Compound 1 induced more mortality earlier than did hexaflumuron.

Ant Studies

Laboratory ant bait studies were carried out with Red Imported Fire Ant (RIFA) (*Solenopsis inivicta*) and Pharaoh Ant (*Monomorium pharionis*). Chitin synthesis inhibitors, such as the compounds of the invention, control ants by killing the molting larvae and/or pupae and potentially preventing the hatching of eggs. Because adult workers are not affected, control is measured by effects on the brood. The studies involved 3–4 day exposure to bait. These limited exposure studies more accurately represent real world bait availability than continuous exposure.

| Compound | Concentration tested | Species | Time to Achieve 50% Brood Reduction | Time to Achieve 90% Brood Reduction* |
|---|---|---|---|---|
| Compound 1 | 0.1%* | RIFA | 2 wks | 3 wks |
| | 0.1% | Pharaoh | 4 wks | NA (70% @ 13 wks) |
| Hexaflumuron | 0.1% | RIFA | NA | NA |
| | 0.25% | RIFA | 4 wks | 10 wks |
| | 0.1% | Pharaoh | NA | NA |

*Only concentration tested.
NA = did not achieve specified percent brood reduction.

Percent brood reduction achieved at end of study listed in parenthesis.

Compound 1 is significantly more potent than hexaflumuron based on a short exposure study with RIFA.

Activity against Daphnia 48 hr exposure to treated water

| Compound | $LC_{50}$ (ppb) in water |
|---|---|
| Compound 1 | 5.0 |
| Compound 2 | >100 |

-continued

| Compound | LC$_{50}$ (ppb) in water |
|---|---|
| Compound 3 | >100 |
| Hexaflumuron | 68.1 |

Compounds 2 and 3, the alkylated derivatives of Compound 1, were much less active against Daphnia than were Compound 1 and hexaflumuron; this is surprising since the activities of Compound 1, 2, and 3 in cockroaches are quite similar.

Formulations

In order to facilitate the application of the compounds of formula (I) to the desired locus, or to facilitate storage, transport or handling, the compound is normally formulated with a carrier and/or a surface-active agent.

A carrier in the present context is any material with which the compound of formula (1) (active ingredient) is formulated to facilitate application to the locus, or storage, transport or handling. A carrier may be a solid or a liquid, including a material which is normally gaseous but which has been compressed to form a liquid. Any of the carriers normally used or known to be usable in formulating insecticidal compositions may be used.

Compositions according to the invention contain 0.0001 to 99.9% by weight active ingredient. Preferably, compositions according to the invention contain 0.001 to 10.0% by weight of active ingredient though proportions as low as 0.0001% may be useful in some circumstances.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulfur; natural and synthetic resins, for example coumaronne resins, polyvinyl chloride, and styrene polymers and copolymers; solid polychlorophenols; bitumen; waxes; agar; and solid fertilizers, for example superphosphates. Cellulose based materials, for example wood, sawdust, agar, paper products, cotton linter, or Methocel®, as well as the other solid carriers that are themselves attractive to or at least non-repellant to termites are particularly suitable and preferable. Mixtures of different solids are often suitable. For example, a mixture of wood flour and agar formulated as a moisture containing solid would be preferable.

Suitable liquid carriers include water; alcohols, for example isopropanol and glycols; ketones, for example acetone, methyl ethyl ketone, methyl isobutyl ketone, isophorone and cyclohexanone; ethers; aromatic or aliphatic hydrocarbons, for example benzene, toluene and xylene; petroleum fractions, for example kerosene and light mineral oils; chlorinated hydrocarbons, for example carbon tetrachloride, perchloroethylene and trichloroethane; polar organic liquids, such as dimethyl formamide, dimethyl acetamide, dimethyl sulfoxide and N-methylpyrrolidone; oils derived from plants, such as corn oil and peanut oil. Mixtures of different liquids are often suitable. for example a mixture of isophorone with a polar organic solvent such as N-methylpyrrolidone, as are mixtures of solid and liquid carriers.

Pesticidal compositions are often formulated and transported in a concentrated form which is subsequently diluted by the user before application. The presence of small amounts of a carrier which is a surface-active agent facilitates this process of dilution. Thus it is suitable to use at least one carrier in such a composition which is a surfaceactive agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sufonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerytlritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide sulfates or sulfonates of these condensation products; alkali or alkaline earth metal salts, preferably sodium salts, or sulfuric or sulfonic acid esters containing at least 10 carbon atoms in the molecule, for example sodium lauryl sulphate, sodium secondary alkyl sulfates, sodium salts of sulfinated castor oil, and sodium alkylaryl sulfonates such as dodecylbenzene sulfonate; and polymers of ethylene oxide and copolymers of ethylene oxide and propylene oxide.

Pesticidal compositions may for example be formulated as wettable powders, dusts, granules, baits, solutions, emulsifiable concentrates, emulsions, suspension concentrates and aerosols.

Wettable powders usually contain 25, 50 or 75% weight of active ingredient and usually contain in addition to solid inert carrier, 3–10% weight of a dispersing agent and, where necessary, 0–10% weight of stabilizer(s) and/or other additives such as penetrants or stickers.

Dusts are usually formulated as a dust concentrate having a similar composition to that of a wettable powder but without a dispersant, and are diluted in the field with further solid cairier to give a composition usually containing 0.5–10% weight of active ingredient.

Granules are usually prepared to have a size between 10 and 100 BS mesh (1.676–0.152 mm), and may be manufactured by, for example, agglomeration or impregnation techniques. Generally, granules will contain 0.01–75% weight active ingredient and 0–10% weight of additives such as stabilizers, surfactants, slow release modifiers and binding agents. The so-called "dry flowable powders" consist of relatively small granules having a relatively high concentration of active ingredient. Of particular interest in current practice are the water dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulation contain 90% or more by weight of finely divided active material, 3–7% by weight of a blend of surfactants, which act as wetting dispersing, suspending and binding agents, and 1–3% by weight of a finely divided carrier, which acts as a resuspending agent.

Baits are prepared by, for example, combining a mixture of a suitable food source, such as sawdust for termites or grain or meal for cockroaches, with an amount of active ingredient sufficient to provide the desired result; for example, from about 0.001% to about 20% weight active ingredient and forming the mixture into a paste by the addition of about 1% to 5% of a water based binder such as agar. The paste-like mixture may be applied as is or may be packed into a housing such as a hollowed out wooden dowel or a plastic tube or bait station. In other embodiments, sheets of paper or cardboard can be sprayed with or dipped in a diluted formulation containing the active ingredient. Baits are a preferable embodiment of the present invention.

Emulsifiable concentrates usually contain, in addition to a solvent and, when necessary, co-solvent, 10–50% weight per volume active ingredient, 2–20% weight per volume emulsifiers and 0–20% weight per volume of other additives such as stabilizers, penetrants and corrosion inhibitors.

Suspension concentrates are usually compounded so as to obtain a stable, non-sedimenting flowable product and usually contain 10–75% weight active ingredient, 0.5–15% weight of dispersing agents, 0.1–10% weight of suspending agents such as protective colloids and thixotropic agents, 0–10% weight of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions are compositions which may be obtained by diluting a wettable powder or a concentrate with water. The said emulsions may be of the water-in-oil or of the oil-in-water type, and may have a thick 'mayonnaise'-like consistency.

The method of applying a compound of Formula (I) to combat termites comprises applying the compound, conveniently in a composition comprising the compound of Formula (I) and a carrier as described above, to a locus or area to be treated for the termites, such as soil or timber, already subject to infestation or attack by termites or intended to be protected from infestation by termites. The active ingredient is, of course, applied in an amount sufficient to effect the desired action of combatting termite infestation. This dosage is dependent upon many factors, including the carrier employed, the method and conditions of the application, whether the formulation is present at the locus in the form of a film, or as discrete particles or as a bait, the thickness of film or size of particles, the degree of termite infestation, and the like.

Proper consideration and resolution of these factors to provide the necessary dosage of the active ingredient at the locus to be protected are within the skill of those versed in the art. In general, however, the effective dosage of the compound of the invention at the locus to be protected—i.e., the dosage to which the termite has access—is of the order of 0.001 to 1.0% based on the total weight of the composition, though under some circumstances the effective concentration may be as little as 0.0001% or as much as 2%, on the same basis.

When used to control cockroaches, it is preferred to use the active ingredient in a treated bait or as a surface treatment.

When used to control ants, it is preferred to use the active ingredient in a liquid bait or granular bait.

When used to control termites, it is preferred to use the active ingredient in a cellulose based bait.

When used to control fleas, it is preferred to use the active ingredient on a treated substrate.

Suitable formulations include granular, paste, or dust cockroach bait, SP or WP cockroach and/or flea sprayables, cellulose-based termite baits, liquid or granular ant baits, feed-through or topical animal treatment for fleas.

We claim:

1. A method of controlling ants which comprises delivering a compound of the formula (I)

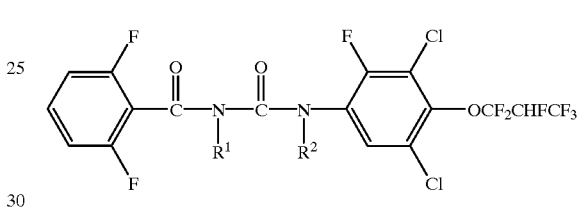

(I)

wherein $R^1$ and $R^2$ are H, methyl, or ethyl, provided that at least one of $R^1$ and $R^2$ is methyl or ethyl, in an amount effective to control ants, to a location where control of ants is desired.

2. An ant bait comprising a compound of the formula

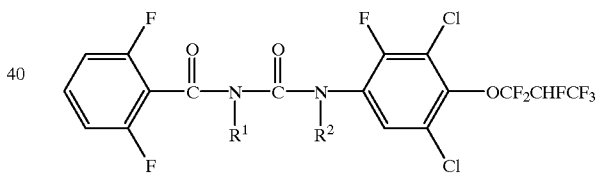

wherein $R^1$ and $R^2$ are independently selected from the group consisting of H, methyl, or ethyl, provided that at least one of $R^1$ and $R^2$ is methyl or ethyl.

3. A method according to claim 1 wherein said compound is part of a treated bait.

4. A ant bait according to claim 2 wherein said ant bait is in a conventional bait.

* * * * *

UNITED STATES PATENT AND TRADEMARK OFFICE
CERTIFICATE OF CORRECTION

PATENT NO. : 6,245,816 B1 Page 1 of 1
DATED : June 12, 2001
INVENTOR(S) : Ronald J. Sbragia, George W. Johnson, Laura L. Karr, Jeff M. Edwards and Brian M. Schneider It is certified that error appears in the above-identified patent and that said Letters Patent is hereby corrected as shown below:

Title page,
Inventors: "Ronald J. Spragia" should read -- Ronald J. Sbragia --.

Signed and Sealed this

Fourteenth Day of May, 2002

*Attest:*

JAMES E. ROGAN
*Attesting Officer*     *Director of the United States Patent and Trademark Office*